United States Patent [19]

Sevrin et al.

[11] Patent Number: 4,931,449
[45] Date of Patent: Jun. 5, 1990

[54] 2-((4-PIPERIDYL)METHYL)BEN-ZOFURO(2,3-C)PYRIDINE DERIVATIVES, AND THEIR APPLICATION IN THERAPY

[75] Inventors: Mireille Sevrin, Paris; Pascal George, Vitry sur Seine; Claude Morel, Cresly Magny les Hameaux, all of France

[73] Assignee: Synthelabo, Paris, France

[21] Appl. No.: 228,747

[22] Filed: Aug. 5, 1988

[30] Foreign Application Priority Data

Aug. 7, 1987 [FR] France .................................. 87 11287

[51] Int. Cl.⁵ ................ C07D 491/048; A61K 31/435
[52] U.S. Cl. ........................................ 514/291; 546/80
[58] Field of Search .................... 546/80, 86; 514/291

[56] References Cited

U.S. PATENT DOCUMENTS 4,604,397 8/1986 Hutchison ........................... 514/291

Primary Examiner—Alan L. Rotman
Attorney, Agent, or Firm—Fleit, Jacobson, Cohn, Price, Holman & Stern

[57] ABSTRACT

A compound of formula (I)

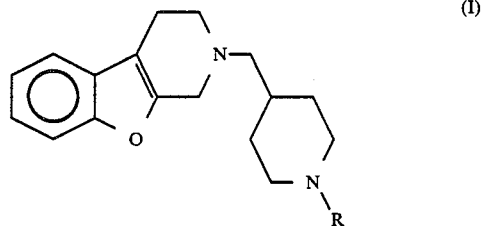

in which R is a benzyl, benzoyl, 3-chlorobenzoyl, 3-methylbenzoyl or ($C_1$–$C_6$ alkoxy)carbonyl group, or a pharmacologically acceptable acid addition salt thereof.

4 Claims, No Drawings

2-((4-PIPERIDYL)METHYL)BENZOFURO(2,3-C)PYRIDINE DERIVATIVES, AND THEIR APPLICATION IN THERAPY

The present invention relates to 2-[(4-piperidyl)methyl]benzofuro[2,3-c]pyridine derivatives, to their preparation, to compositions containing them and to their use in therapy.

The present invention provides a compound of formula

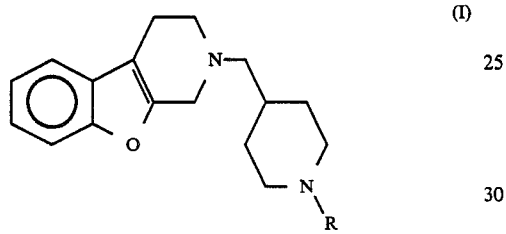

in which R is a benzyl, benzoyl, 3-chlorobenzoyl, 3-methylbenzoyl or ($C_1$–$C_6$ alkoxy)carbonyl group, or a pharmacologically acceptable acid addition salt thereof.

The ($C_1$–$C_6$ alkoxy)carbonyl may be, for example, ethoxycarbonyl.

The compounds of formula (I) may be prepared by a process as illustrated in scheme 1 on the following page.

The present invention provides a process for preparing a compound of formula (I), or a pharmacologically acceptable salt thereof, wherein R is a benzyl group, wherein 2-[(1-benzyl-4-piperidyl)carbonyl]-1,2,3,4-tetrahydrobenzofuro[2,3-c]pyridine of formula (V) is reduced with a simple or complex boron hydride, such as diborane or a borane/methyl sulphide complex, or with lithium aluminium hydride, in an ethereal solvent such as diethyl ether, tetrahydrofuran or dioxane at a temperature of from 20° to 100° C., and if desired, preparing a pharmacologically acceptable salt of the compound thus obtained.

Scheme 1

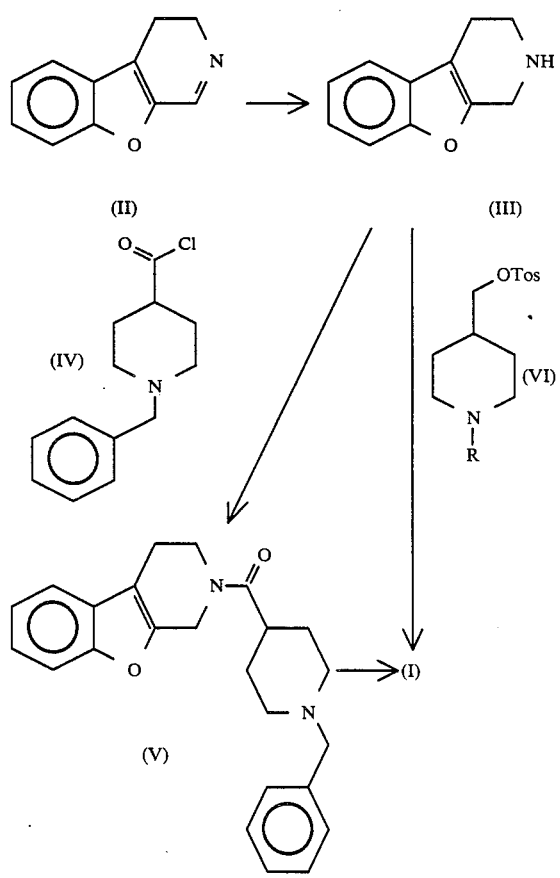

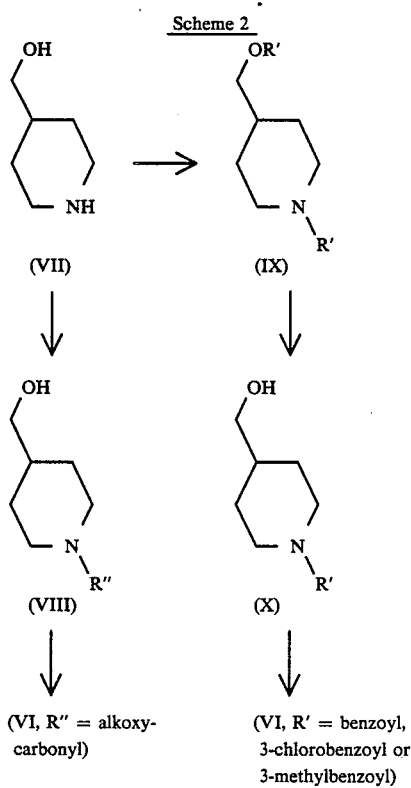

Scheme 2

(VI, R" = alkoxy-carbonyl)

(VI, R' = benzoyl, 3-chlorobenzoyl or 3-methylbenzoyl)

The compound of formula (V) may be prepared by reacting 1,2,3,4-tetrahydrobenzofuro[2,3-c]pyridine of formula (III) with 1-benzyl-4-piperidinecarboxylic acid chloride of formula (IV), prepared in situ from the corresponding acid and a chlorinating agent such as thionyl chloride, in an inert solvent, such as dichloromethane, in the presence of a base, such as N,N-dimethylanaline, at a temperature of from 20° to 40° C.

The compound of formula (III) may be prepared by reducing 3,4-dihydrobenzofuro[2,3-c]pyridine of formula (II), described in EP-A-0,204,254, with an alkali metal borohydride, such as sodium borohydride, in a lower aliphatic solvent, such as methanol, at a temperature of from 20° to 40° C.

The present invention also provides a process for preparing a compound of formula (I) or a pharmacologically acceptable salt thereof, wherein R is a benzoyl, 3-chlorobenzoyl, 3-methylbenzoyl or ($C_1$-$C_6$ alkoxy) carbonyl group, wherein 1,2,3,4-tetrahydrobenzofuro[2,3-c]pyridine of formula (III) is reacted with a tosylate of formula (VI), in which Tos is a tosyl group and R is a benzoyl, 3-chlorobenzoyl, 3-methylbenzoyl or ($C_1$-$C_6$ alkoxy) carbonyl group, in the absence or presence of an inert solvent such as dimethylformamide or xylene, at a temperature of from 20° to 150° C., and if desired, preparing a pharmacologically acceptable salt of the compound thus obtained. An organic base, for example a tertiary amine, or an inorganic base, for example an alkali metal carbonate or hydrogen carbonate, may be present.

The tosylate of formula (VI) may be prepared according to the method illustrated in Scheme 2.

When R is a benzoyl, 3-chlorobenzoyl or 3-methylbenzoyl group, 4-piperidinemethanol of formula (VII) is reacted with benzoic acid chloride, 3-chlorobenzoic acid chloride or 3-methylbenzoic acid chloride, in an inert solvent, such as a chlorinated solvent, at a temperature of 20° to 80° C. An ester amide of formula (IX) is thereby obtained, which is saponified, for example with sodium hydroxide or potassium hydroxide, in a lower aliphatic alcohol solvent, preferably ethanol, to obtain an alcohol of formula (X), the tosylate of which is prepared by reacting it with tosyl chloride in a basic medium, such as pyridine.

When R is a ($C_1$-$C_6$ alkoxy)carbonyl group, 4-piperidinemethanol of formula (VII) is reacted with a $C_1$-$C_6$ alkyl chloroformate in a solvent, such as a chlorinated solvent, at room temperature. A carbamate of formula (VIII) is thereby obtained, the tosylate of which is prepared as described above.

4-Piperidinemethanol of formula (VII) may be obtained, for example, by the reduction of ethyl 4-piperidinecarboxylate with lithium aluminium hydride, or alternatively by the reduction of ethyl 1-benzyl-4-piperidinecarboxylate in the same manner, followed by catalytic hydrogenolysis under pressure.

The compound of formula (I) in which R is a benzyl group can obviously also be obtained by the reduction of a compound of formula (I) in which R denotes a benzoyl group, under the conditions described in relation to the reduction of the compound of formula (V).

The salts of the compounds of formula (I) may be prepared in a conventional manner.

The Examples which follow further illustrate the present invention. The microanalyses and the IR and NMR spectra confirm the structures of the compounds obtained. The numbers given in brackets in the titles of the Examples correspond to those in the table given later.

EXAMPLE 1

Compound No. 1

2-[(1-Benzyl-4-piperidyl)methyl]-1,2,3,4-tetrahydrobenzofuro[2,3-c]pyridine dihydrochloride.

1.1 1,2,3,4-Tetrahydrobenzofuro[2,3-c]pyridine hydrochloride 9.2 g (240 mmol) of sodium borohydride are added in small portions and in the space of 3 h to a suspension of 8.2 g (47.8 mmol) of 3,4-dihydrobenzofuro[2,3-c]pyridine in 350 ml of methanol. The mixture is stirred for 20 h at 20° C. and the solvent then evaporated off under reduced pressure. The residue is washed with water and the 1,2,3,4-tetrahydrobenzofuro[2,3-c]pyridine extracted by means of ethyl acetate. The organic phase is separated off after settling has taken place, dried over sodium sulphale and evaporated under reduced pressure, and the residue is treated with one equivalent of 0.1N hydrochloric acid in isopropyl alcohol. The hydrochloride is isolated and recrystallized in a mixture of isopropyl alcohol and ethanol.

Melting point: 289°–291° C.

1.2

2-[(1-Benzyl-4-piperidyl)carbonyl]-1,2,3,4-tetrahydrobenzofuro[2,3-c]pyridine hydrochloride.

4.4 g (20 mmol) of 1-benzyl-4-piperidinecarboxylic acid are added to 12 ml (165 mmol) of thionyl chloride, and the mixture is stirred under an inert atmosphere. Stirring is maintained for 16 h at 20° C., and the excess thionyl chloride is then evaporated off under reduced pressure. The residue is taken up with 25 ml of toluene and the mixture again evaporated under reduced pressure. The solid residue is dissolved in dichloromethane, and 5.7 ml (45 mmol) of N,N-dimethylaniline and 3.4 g (20 mmol) of 1,2,3,4-tetrahydrobenzofuro[2,3-c]pyridine (base), dissolved in 12 ml of dichloromethane, are added under argon. The mixture is stirred for 2 h at 20° C. and then poured into water. The insoluble material is isolated by filtration, washed with water and suspended in a mixture of water and ethyl acetate. This suspension is treated with ammonia solution, and the organic phase is separated off after settling has taken place, washed with water and dried. The solvent is evaporated off under reduced pressure and the amide thereby obtained dried under vacuum. The hydrochloride of the latter is prepared in 0.1N hydrochloric acid in isopropyl alcohol, and recrystallized in ethanol.

Melting point: 226°–228° C.

1.3
2-[(1-Benzyl-4-piperidyl)methyl]-1,2,3,4-tetrahydrobenzofuro[2,3-c]pyridine dihydrochloride 2.5 g (6.7 mmol) of 2-[(1-benzyl-4-piperidyl)-carbonyl]-1,2,3,4-tetrahydrobenzofuro[2,3-c]pyridine (base) are added, with stirring and at 20° C., to a suspension of 0.4 g (10 mmol) of lithium aluminium hydride in 120 ml of diethyl ether, and the mixture is then heated under reflux for 4 h. The mixture is cooled and hydrolysed, the insoluble material is filtered off and the filtrate is evaporated under reduced pressure. The residue is dried under vacuum and 2.3 g of solid are collected. Melting point: 107°–109° C. The dihydrochloride of this compound is prepared by means of 0.1N hydrochloric acid in isopropyl alcohol and recrystallized in a mixture of methanol and ethanol.

Melting point: 285°–288° C.

EXAMPLE 2

Compound No. 4

2-{[1-(3-Methylbenzoyl)-4-piperidyl]methyl}-1,2,3,4-benzofuro[2,3-c]pyridine benzenesulphonate

2.1 4-Piperidinemethanol.

28.5 g (0.75 mol) of lithium aluminium hydride and 1.2 l of tetrahydrofuran are introduced into a 4-l three-necked round-bottomed flask equipped with a mechanical stirring system and a condenser. 117.9 g (0.75 mol) of ethyl 4-piperidinecarboxylate dissolved in 1.2 l of tetrahydrofuran are added to the suspension obtained, and the mixture is stirred for 6 h at 20° C. It is cooled to 0° C., and then hydrolysed by adding successively 22 ml of water, 22 ml of 1N sodium hydroxide and 46 ml of water. The mixture is stirred for 30 min. at 20° C. and filtered, and the precipitate is washed with tetrahydrofuran and then with ether. The solvents are evaporated off under reduced pressure and 84.4 g of an oil are obtained, this being used without further treatment in the following stage.

2.2.[1-(3-Methylbenzoyl)-4-piperidyl]methyl 3-methylbenzoate.

42.25 g (0.367 mol) of 4-piperidinemethanol and 430 ml of 1,2-dichloroethane are introduced under an argon atmosphere into a 3-l three-necked round-bottomed flask, and 82 g (0.81 mol) of triethylamine are added, followed by 125.2 g (0.81 mol) of 3-methylbenzoyl chloride. The mixture is heated under reflux for 4h 30 min., a further 8.2 g (0.08 mol) of triethylamine and 12.5 g (0.08 mol) of 3-methylbenzoyl chloride are added, and the mixture is heated for a further 3h.

It is filtered, the salts are washed with 1,2-dichloroethane, the filtrate is evaporated under reduced pressure, the residue is dissolved in ethyl acetate, the solution is washed with saturated aqueous sodium chloride solution, the solvent is evaporated off under reduced pressure and the residue is recrystallized in a 1:1 isopropyl alcohol/ethyl acetate mixture. 80 g of white solid are obtained.

Melting point: 80°–83° C.

2.3. 1-(3-Methylbenzoyl)-4-piperidinemethanol.

A solution of 12.76 g (0.23 mol) of potassium hydroxide in 75 ml of ethanol and 75 ml of water is added to a solution of 80 g (0.23 mol) of [1-(3-methylbenzoyl)-4-piperidyl]methyl 3-methylbenzoate in 400 ml of ethanol. The mixture is stirred at 20° C. for 3h, the solvent evaporated off under reduced pressure and the aqueous phase extracted with ethyl acetate. The organic phase is washed with water and then with saturated aqueous sodium chloride solution, and dried over magnesium sulphate. The solvent is evaporated off under reduced pressure and 53 g of alcohol are obtained, this being used without further treatment in the following stage.

2.4 [1-(3-Methylbenzoyl)-4-piperidyl]methyl 4-methylbenzenesulphonate.

53.3 g (0.28 mol) of 4-methylbenzenesulphonyl chloride in 60 ml of pyridine are added to a solution of 52 g (0.22 mol) of 1-(3-methylbenzoyl)-4-piperidinemethanol in 100 ml of pyridine. The mixture is stirred at 20° C. for 4 h, and then poured into ice. The phase is extracted with dichloromethane, and the organic phase washed with 5N aqueous hydrochloric acid solution and dried over magnesium sulphate. The solvents are evaporated off under reduced pressure and 70 g of white solid are obtained.

Melting point: 68°–70° C.

2.5 2-{[1-(3-Methylbenzoyl)-4-piperidyl]methyl}-1,2,3,4-benzofuro[2,3-c]pyridine benzenesulphonate.

1.1 g (6.3 mmol) of 1,2,3,4-tetrahydrobenzofuro-[2,3-c]pyridine, 2.7 g (7 mmol) of [1-(3-methylbenzoyl)-4-piperidyl]methyl 4-methylbenzenesulphonate, 1.93 g of potassium carbonate and 10 ml of dimethylformamide are introduced into a round-bottomed flask equipped with a magnetic stirrer and placed under argon. The mixture is stirred for 5 h at 120° C. and then 12 h at 20° C. The mixture is poured onto ice and extracted with ethyl acetate, the organic phase is washed with water and then with saturated sodium chloride solution and dried over magnesium sulphate, the solvent is evaporated off under reduced pressure and the residue is purified by chromatography on a silica column, eluting with ether. 0.8 g of base is thereby obtained.

0.6 g (1.51 mmol) of this is dissolved in 30 ml of ethanol, a solution of 0.239 g (1.51 mmol) of benzenesulphonic acid is added, the mixture is stirred for 30 min, the solvent is evaporated off under reduced pressure, and the residue is stirred in ethyl acetate, filtered off and dried. 0.71 g of benzenesulphonate is finally isolated.

Melting point: 166°–169° C.

EXAMPLE 3

Compound No. 5

Ethyl 4-[(1,2,3,4-tetrahydrobenzofuro[2,3-c]pyrid-2-yl)-methyl]-1-piperidinecarboxylate fumarate.

3.1 1-Benzyl-4-piperidinemethanol hydrochloride.

117 g (473 mmol) of ethyl 1-benzyl-4-piperidinecarboxylate dissolved in 1.5 l of ether are added under argon to a suspension of 18 g (473 mmol) of lithium aluminium hydride in 1 l of ether. The mixture is stirred at 20° C. for 1 h, then hydrolysed with 34 ml of water and filtered, the solid being rinsed with ether, and a stream of hydrogen chloride gas is bubbled through the filtrate. 105.4 g of hydrochloride are obtained. Melting point: 181.5°–185° C.

3.2 4-Piperidinemethanol hydrochloride.

105 g of 1-benzyl-4-piperidinemethanol hydrochloride, 2 l of ethanol and 12.5 g of palladinized charcoal are introduced into a Parr bottle, and a hydrogenolysis is performed at 50° C. under a pressure of 0.4 MPa. The mixture is filtered and the filtrate evaporated off under reduced pressure. 58.7 g of solid are obtained. Melting point: 128°–130° C.

3.3 Ethyl 4-hydroxymethyl-1-piperidinecarboxylate.

168.3 g (1.22 mol) of potassium carbonate are added to a solution of 61.6 g (406 mmol) of 4-piperidinemethanol hydrochloride in a mixture of 406 ml of chloroform and 406 ml of water, followed by 42.55 ml (440 mmol) of ethyl chloroformate dissolved in 160 ml of chloroform. The mixture is stirred for 3 h at 20° C., the organic phase is separated off, the aqueous phase is extracted with dichloromethane, the organic phases are combined to form a single phase, washed with water and dried over magnesium sulphate, and the solvents are evaporated off under reduced pressure. 76 g of an oil is obtained, this being used without further treatment in the following stage.

3.4 Ethyl 4-[(4-methylphensulphonyloxy)methyl]-1-piperidinecarboxylate.

86.9 g (456 mmol) of 4-methylbenzenesulphonyl chloride dissolved in 81 ml of pyridine are added to a solution of 71.3 g (380 mmol) of ethyl 4-hydroxymethyl-1-piperidinecarboxylate in 57 ml of pyridine. The mixture is stirred for 12 h at 20° C., poured into ice-cold water and extracted with ether, the organic phase is separated off, washed with water and then with dilute hydrochloric acid solution and dried over magnesium sulphate, the solvent is evaporated off under reduced pressure and the residue is recrystallized in cyclohexane. 123 g of white solid are obtained. Melting point: 65°–66° C.

3.5 Ethyl 4-[(1,2,3,4-tetrahydrobenzofuro[2,3-c]pyrid-2-yl)methyl]-1-piperidinecarboxylate fumarate.

2.8 g (20 mmol) of potassium carbonate and 3.4 g (10 mmol) of ethyl 4-[(4-methylphenylsulphonyloxy)methyl]-1-piperidinecarboxylate are added to a solution 1.7 g (10 mmol) of 1,2,3,4-tetrahydrobenzofuro[2,3-c]pyridine (base) dissolved in 30 ml of xylene. The suspension is heated for 26 h to 140° C. and then cooled. The insoluble material is then filtered off, the filtrate concentrated under reduced pressure and the residue purified by chromatography on a silica column. The fumarate of this compound is prepared in ethanol and recrystallized in acetone. 3.4 g of yellow solid are thereby obtained. Melting point: 167°–170° C.

The table below illustrates the chemical structures and physical properties of a few compounds according to the invention.

TABLE

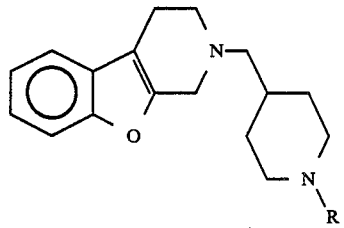

(I)

| No | R | Salt | M.p. (°C.) |
|----|---|------|------------|
| 1 | $C_6H_5$—$CH_2$— | dihydrochloride | 285–288 |
| 2 | $C_6H_5$—CO— | benzenesulphonate | 203–204 |
| 3 | 3-Cl—$C_6H_4$—CO— | benzenesulphonate | 166–168 |
| 4 | 3-$CH_3$—$C_6H_4$—CO— | benzenesulphonate hemihydrate | 166–169 |
| 5 | $C_2H_5$—O—CO— | fumarate | 167–170 |

The compounds of the invention were subjected to a series of pharmacological tests which demonstrated their value as substances having therapeutic activity.

Thus, they were subjected to a study in respect of their affinity for 5-$HT_{1A}$ type serotoninergic receptors. In the rat hippocampus, the compounds displace a labelled specific ligand, [$^3$H]-8-hydroxy-2-dipropylaminotetral in, (hereinafter designated "[$^3$H]-8-OH-DPAT"), described by Gozlan et al, Nature, (1983), 305, 140–142.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed three times at 4° C. by centrifuging them on each occasion at 48,000×g and resuspending the pellet for 10 min. in cooled fresh buffer. Finally, the last pellet is suspended in the buffer to produce a concentration of 100 mg of original tissue per ml of 50 mM buffer. The suspension is then left to incubate at 37° C. for 10 min.

The binding with [$^3$H]-8-OH-DPAT is determined by incubating 10 μl of membrane suspension in a final volume of 1 ml of buffer containing 10 μl pargyline.

After the incubation, the membranes are recovered by filtration on Whatman GF/B filters, which are washed three times with 5-ml aliquot portions of ice-cold buffer. The filters are extracted in scintillation fluid and their radioactivity is measured by liquid scintigraphy. The specific binding of [$^3$H]-8-OH-DPAT is defined as the quantity of radioactivity retained on the filters and capable of being inhibited by coincubation in 10 μM 5-hydroxytryptamine. At a [$^3$H]-8-OH-DPAT concentration of 1 nM, the specific binding represents from 70 to 80% of the total radioactivity recovered on the filter.

For each concentration of test compound, the percentage inhibition of the binding with [$^3$H]-8-OH- DPAT, and then the IC$_{50}$ concentration, the concentration which inhibits 50% of the binding, are determined.

For the compounds of the invention, the IC$_{50}$ values lie between 0.001 and 0.3 μM.

The central activity of the compounds of the invention was assessed by their effects on the "PGO (pontogeniculoocipital) spikes" induced by reserpine (PGO-R test) in cats, according to the method described by H. Depoortere, Sleep 1976, 3rd Europ. Congr. Sleep Res., Montpellier 1976, 358–361 (Karger, Basel 1977).

Cumulative doses of test compounds are administered (from 0.01 to 3 mg/kg intravenously) at 30-min. time intervals, 4h after the intraperitoneal injection of a dose of 0.75 mg/kg of reserpine, to curarized cats under artificial ventilation. The electroencephalographic and phasic (PGO-R spike) activities are obtained using cortical and deep (lateral geniculate) electrodes. For each dose of test compound, the percentage decrease in the number of PGO spikes, and then the AD$_{50}$, the active dose which decreases this number of spikes by 50%, are determined.

For the compounds of the invention, the intravenous ED$_{50}$ values lie between 0.01 and 1 mg/kg.

The results of the tests show that the compounds of general formula (I) possess, in vitro, a high affinity and a selectivity for 5-HT$_{1A}$ type serotoninergic receptors. In vivo, they show either an agonist, or a partial agonist or an antagonist activity with respect to these receptors.

The compounds of the invention may hence be used for the treatment of diseases and conditions directly or indirectly involving the 5-HT$_{1A}$ type serotoninergic receptors, in particular for the treatment of depressive states, anxiety states and sleep disorders, in the regulation of food intake and also for the treatment of vascular, cerebrovascular or cardiovascular disorders such as migraine or hypertension.

Thus the present invention provides a compound of formula (I), or a pharmacologically acceptable salt thereof, for use in a method of treatment of the human or animal body by therapy. The present invention also provides a compound of formula (I), or a pharmacologically acceptable salt thereof, for use in a method of treatment of a depressive state, anxiety state, sleep disorder, cerebrovascular disorder or cardiovascular disorder or for the regulation of food intake. The present invention additionally provides the use of a compound of formula (I), or a pharmacologically acceptable salt thereof, in the manufacture of a medicament for the treatment of a depressive state, anxiety state, sleep disorder, vascular disorder, cerebrovascular disorder or cardiovascular disorder or for the regulation of food intake. The daily dosage is generally from 1 to 1,000 mg.

The present invention finally provides a pharmaceutical composition comprising a compound of formula (I), or a pharmacologically acceptable acid addition salt thereof, and a pharmaceutically acceptable excipient. The composition may be in a form suitable for oral or parenteral administration.

We claim:

1. A compound of formula (I)

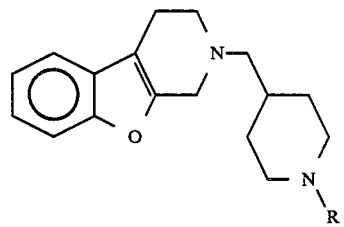

in which R is a benzyl, benzoyl, 3-chlorobenzoyl, 3-methylbenzoyl or (C$_1$–C$_6$ alkoxy)carbonyl group, or a pharmacologically acceptable acid addition salt thereof.

2. A pharmaceutical composition comprising a pharmaceutically effective amount of a compound of formula (I) as defined in claim 1, or a pharmacologically acceptable acid addition salt thereof, and a pharmaceutically acceptable excipient.

3. A method of treatment of a depressive state or anxiety state which comprises administering to a subject suffering or liable to suffer therefrom an effective amount of a compound of formula (I) as defined in claim 1, or a pharmacologically acceptable salt thereof.

4. A method of treatment of hypertension which comprises administering to a subject suffering or liable to suffer therefrom an effective amount of a compound of formula (I) as defined in claim 1, or a pharmacologically acceptable salt thereof.

* * * * *